United States Patent [19]

Masuda

[11] Patent Number: 5,143,845

[45] Date of Patent: * Sep. 1, 1992

[54] MIXTURE OF SACCARIFYING LACTIC ACID PRODUCING AND BUTYRIC ACID PRODUCING BACTERIA

[75] Inventor: Takashi Masuda, Tokyo, Japan

[73] Assignee: Toa Pharmaceutical Co., Ltd., Tokyo, Japan

[*] Notice: The portion of the term of this patent subsequent to Feb. 28, 2006 has been disclaimed.

[21] Appl. No.: 616,820

[22] Filed: Nov. 16, 1990

Related U.S. Application Data

[63] Continuation of Ser. No. 86,951, Aug. 19, 1987, abandoned.

[30] Foreign Application Priority Data

Sep. 3, 1986 [JP] Japan ................... 61-206018
Oct. 6, 1986 [JP] Japan ................... 61-236073

[51] Int. Cl.$^5$ ................... C12N 1/20
[52] U.S. Cl. ................... 435/252.4; 435/252.5; 435/252.7; 435/252.9; 435/253.4; 435/832; 435/842; 435/885; 424/93 C
[58] Field of Search ................... 424/93

[56] References Cited

U.S. PATENT DOCUMENTS

| | | | |
|---|---|---|---|
| 1,927,813 | 9/1933 | Legg | 435/42 |
| 3,767,534 | 10/1973 | Miura | 435/813 |
| 4,689,226 | 8/1987 | Nurmi | 435/252.9 |
| 4,808,417 | 2/1989 | Masuda | 426/807 |

FOREIGN PATENT DOCUMENTS

2491495 4/1982 France ................... 435/42

OTHER PUBLICATIONS

Biological Abstracts, vol. 63, No. 2, Jan. 15, 1977, p. 9163, Abs. No. 9157, Morishita, "Microorganisms responsible for controlling the populations of *Escherichie coli* et al., and enterococeus and the consistency of cecal contents in the chicken".

*Primary Examiner*—Douglas W. Robinson
*Assistant Examiner*—Marian C. Knode
*Attorney, Agent, or Firm*—Akoo-Toren

[57] ABSTRACT

A mixture of three kinds of bacteria is disclosed which is useful for humans and animals. The symbiotic mixture contains as effective ingredients lactic acid producing bacteria, saccarificating bacteria, and butyric acid producing bacteria which are useful for human and animals. A method is disclosed for effectively cultivating a symbiotic mixture of these three kinds of bacteria by a cooperative action.

4 Claims, 1 Drawing Sheet

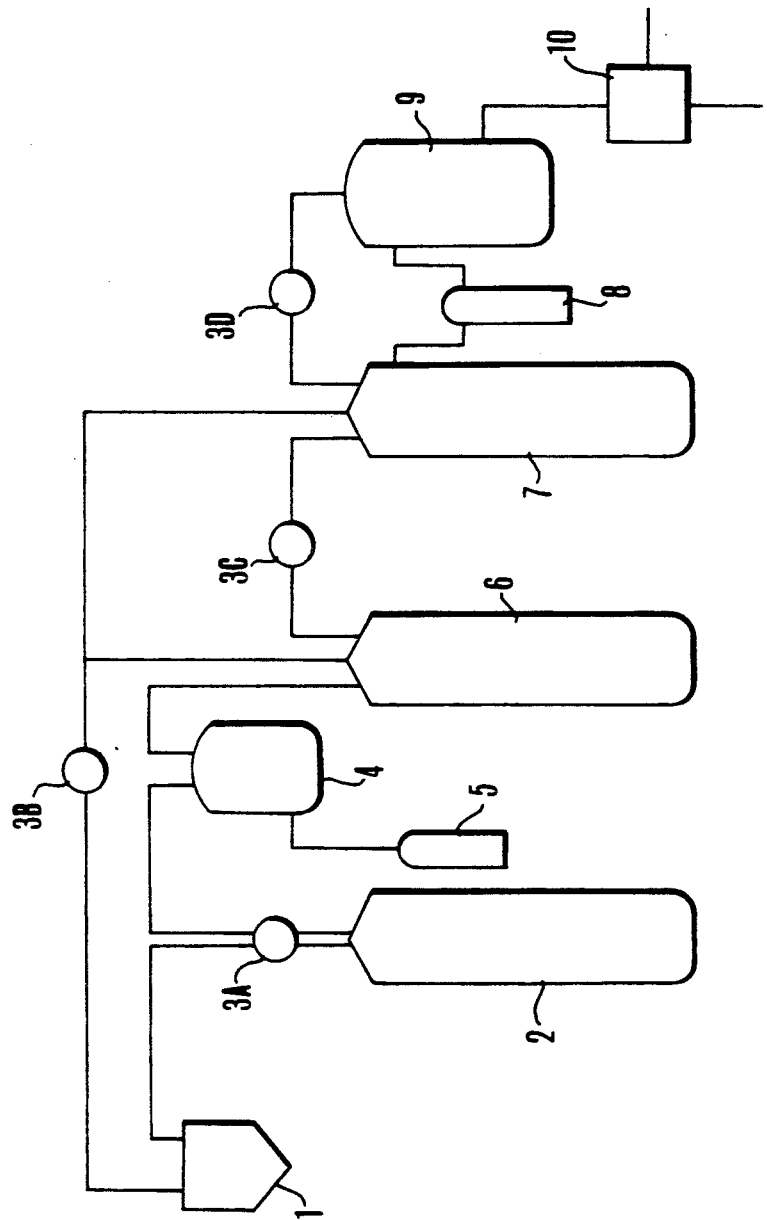

MIXTURE OF SACCARIFYING LACTIC ACID PRODUCING AND BUTYRIC ACID PRODUCING BACTERIA

This is a continuation of application Ser. No. 07/086,951, filed Aug. 19, 1987, now abandoned.

BACKGROUND OF THE INVENTION

1. Field of the Invention

The present invention relates to a symbiotic mixture of activated bacteria and to a method for cultivation thereof. More particularly, this invention concerns a symbiotic mixture of three kinds of bacteria consisting of lactic acid producing bacteria (hereinafter called LB), saccarificating bacteria (SB), and butyric acid producing bacteria (BB). which are useful for human and animals, and to a method for effectively cultivating a symbiotic mixture of these three kinds of bacteria by a cooperative action.

Activated bacteria have played an important role in each field of applied microbiological industries. In the case of oral administration to humans or animals of a mixture of two or more kinds of activated bacteria, symbiosis of microorganisms in a living body, especially within the digestive tract may occur, or coexisting microorganisms may exert a profitable influence on each other. However, there are only a few products which involve the application of active symbiosis.

The present inventor has aimed, for a long time at the application of a symbiotic mixture of activated bacteria, which brings about symbiosis. After making various investigations, he prepared a symbiotic mixture of three kinds of bacteria comprising LB, SB, and BB, and succeeded in applying it as a raw material to fields such as a medicament, food for improving human health, and feed for fishes and livestock. Furthermore, the present inventor found a method for efficiently cultivating these three kinds of bacteria by the use of cooperative action.

SUMMARY OF THE INVENTION

The symbiotic mixture according to the present invention contains as effective ingredients lactic acid producing bacteria, saccarificating bacteria, and butyric acid producing bacteria which are useful for human and animals. Further, the method for cultivating the three kinds of bacteria according to the present invention comprises proliferating saccarificating bacteria in a culture medium containing a protein as the source of nitrogen and a carbohydrate as the source of carbon; filtering the thus obtained culture fluid to remove the saccarificating bacteria and introducing the filtrate to a fresh culture medium, in which lactic acid producing bacteria are cultured under aerobic conditions. The method for cultivating three kinds of bacteria according to the invention further includes proliferating both lactic acid producing bacteria and butyric acid producing bacteria under anaerobic conditions in the fresh medium containing the culture fluid from the culture of the lactic acid producing bacteria. Also according to the method of the invention, the lactic acid producing bacteria and butyric acid producing bacteria are segmented from the culture medium after the spore formation of butyric acid producing bacteria.

DETAILED DESCRIPTION OF THE INVENTION

The fact that the symbiotic mixture of three kinds of bacteria according to the present invention shows the tendency to promote their own growth in a living body by the cooperative action has been proved by the following experimental results.

1) Symbiosis between SB and LB

When LB was cultured either in a medium alone or in the medium containing the filtrate of culture fluid of SB, the LB count in the latter was shown to be about 100 times higher than in former. This mechanism is considered to be based on the phenomenon that protease and amylase produced during the cultivation of SB decompose the protein and carbohydrate in a circumstance (e.g. in the medium or in a living body) to supply amino acids (e.g. glutamic acid, aspartic acid) and glucose, respectively, necessary for growth of LB, thus promoting the proliferation of LB.

2) Symbiosis between LB and BB

Compared with the respective bacteria count proliferated in both single culture and mixed culture of both bacteria, the BB count in the latter was observed to be about 10 times higher than in the former and also the LB count in the latter several times higher than in the former. A possible explanation for this mechanism is that in the course of cultivation respective bacteria will produce a growth promoting factor which is useful for each other.

The following LB are suitable for a constructive member of the symbiotic mixture of three kinds of bacterial in the present invention:

*Streptococcus faecalis, Streptococcus faecium, Streptococcus lactis, Streptococcus thermophilus,*

*Lactobacillus bulgaricus, Lactobacillus jugurt, Lactobacillus acidophilus, Lactobacillus plantarum, Lactobacillus bifidus,*

*Bifidobacterium bifidum, Bifidobacterium infantis, Bifidobacterium longum,* examples of SB are as follows:

*Bacillus mesentericus, Bacillus subtilis, Bacillus natto,* examples of BB are as follows:

*Clostridium butyricum, Clostridium acetobutyricum.*

In the pharmaceutical preparation of the symbiotic mixture of three kinds of bacteria, potato starch, corn starch, lactose, and refined sugar are suitably employed, single or combined, as a vehicle.

Three kinds of activated bacteria are prepared as active principles containing $10^6$–$10^{10}$/g and then mixed. The ratio to be mixed is preferably 1 to 8 parts of SB or BB against 1 part of LB.

Incidentally, when SB and BB are employed after the spore formation, their heat stability, dry stability, and drug stability are enhanced.

BRIEF DESCRIPTION OF DRAWING

The drawing is a flow diagram for practice of the present invention.

DETAILED DESCRIPTION OF THE PREFERRED EMBODIMENTS

The present invention will be better understood from the following preferred embodiments.

EXAMPLE 1

The embodiment of the present symbiotic mixture of three kinds of bacteria as a medicament for bowel movement (pharmaceutical medicament) will be described hereinafter.

(1) Kinds of activated bacteria

*Streptococcus faecalis* T-110 for LB (in accordance with the Treaty of Budapest, it was deposited with the international deposit agency in Japan, Fermentation Research Institute, Agency of Industrial Science and Technology, Ministry of International Trade and Industry, Deposition No. 8936),

*Bacillus mesentericus* TO-A for SB (Deposition No. 8934),

*Clostridium butyricum* TO-A for BB (Deposition No. 8935).

(2) Bacteria count of respective active principles, vehicles, and the ratio of mixture:

| Active principle of LB (5 × $10^8$/g) | 1 part |
|---|---|
| Active principle of SB (spore) (5 × $10^6$/g) | 5 parts |
| Active principle of BB (spore) (5 × $10^7$/g) | 5 parts |
| Lactose | 40 parts |
| Potato starch | 49 parts |

(3) In case that the mixture of three kinds of bacteria pharmaceutically prepared as mentioned above is employed as a medicament for bowel movement, the pharmacological action against intestinal flora will be illustrated hereinafter.

Administration Example 1

Change in the intestinal flora after oral administration in the rat was compared with that in a control group, an extreme increase in bifidobacterium and decrease in *Escherichia coli* being observed in the administered group.

Administration Example 2

After the medicament was administered orally in the rat, the intestinal pH was compared with that in a control group. The pH in the intestinal tracts decreased significantly in the administered group. This fact will suggest that the medicament has an effect of growth inhibition to harmful bacteria.

Administration Example 3

After the medicament was administered orally to the bottle-fed infants for 2 weeks, the variation of fecal bifidobacterium was observed, a significant increase in bifidobacterium being shown.

Administration Example 4

When the medicament was orally administered to the patients of acute enteritis and habitual obstipation at a dose of 3 g/day for 1 to 7 days, effective results were obtained and in the group where antibiotics were administered the appearance of change of normal bacterial flora was not observed.

As mentioned above, when the symbiotic mixture of three kinds of bacteria related to the present invention is applied to a pharmacological preparation, food for maintaining health, and feeds as a main raw material, it produces symbiosis especially in the digestive tract, after oral administration, under the aforesaid mechanism and hence satisfactory effects will be obtained on maintenance and recovery of the intestinal flora.

Another invention or a method for the cultivation of three kinds of bacteria will be described in detail hereinafter.

A method for cultivation of the three kinds of bacteria present in the composition of the invention is composed of characteristic procedures, in which SB are proliferated in a culture medium consisting of a protein as the source of nitrogen and a carbohydrate as the source of carbon and filtered to obtain the filtrate. In a fresh medium supplemented with the filtrate, LB are cultured under aerobic conditions. Further in a fresh medium containing the culture fluid of LB, both LB and BB are cultured under anaerobic conditions, and after the spore formation of BB the mixture of LB and BB is separated from the culture fluid.

The method for cultivation related to the present invention enables three kinds of bacteria to proliferate effectively by symbiosis and will ensure an increase in bacteria count as compared with a single culture of respective bacteria.

Examples of SB, LB, and BB applicable to the method of the present invention are the same as mentioned above.

The cultivation of three kinds of bacteria is accomplished in the basal medium containing a protein and carbohydrate as the source of nitrogen and carbon, respectively. For the protein as the source of nitrogen, a natural or crude protein (processed in some degree) is available, hence the cost of a raw material for the medium is low and economical. Examples are corn steep liquor, fish liver, and milk casein. For the carbodyrate as the source of carbon, potato starch, corn starch, and soluble starch can be used.

Embodiment of the present invention will be described hereinafter according to the individual process.

The First Process

First of all SB are proliferated in the medium (hereinafter called a basal medium) consisting of a protein as the source of nitrogen and a carbohydrate as the source of carbon. Cultivation is accomplished under an aerobic condition and cultivating temperature ranges 25° C. to 40° C., preferable about 37° C. A period of cultivation is usually for 4 to 10 hours. After finishing cultivation, the SB are separated (e.g. filtration) from the culture fluid to obtain a filtrate and then spore formation is carried out according to the usual method.

The Second Process

Subsequently, the filtrate is added to the aforesaid basal medium, and LB is inoculated and proliferated. The conditions for cultivation are the same as in the first process. The quantity to be added of the filtrate obtained from the culture fluid of SB ranges preferably from 0.25 percent to 10.0 percent of the basal medium. In the filtrate from the culture fluid of SB there exist amino acids, glucose, and other products, which are produced by SB due to the metabolism of proteins and carbohydrates, and then LB will gain the products as nutrients, hence the proliferation of LB is promoted. Therefore, the raw materials of high cost, such as a broth, peptone, and yeast extract, which are necessary for the single cultivation of LB, will not be needed.

The Third Process

After cultivation of LB in the second process, the culture fluid containing LB is added into the basal medium, in which BB are inoculated and cultured together with LB under anaerobic conditions and temperature ranges of 25° C. to 40° C., preferably about 37° C. The cultivation is followed by the spore formation of BB, by which BB are provided with heat stability, and then LB and BB are separated from the culture fluid.

The method of the invention can be carried out continuously; to will be illustrated in the accompanying drawing, which is a process diagram for explaining the operation procedure of the present invention. The sterilized basal medium is supplied by the medium delivery pump 3A from the medium tank 1 to the culture tank 2 for proliferating SB. The culture fluid in the culture tank 2 in which SB are proliferated is transferred to the separation tank 4, in which SB are separated, by the delivery pump 3A. By equalizing the quantity of the basal medium to be supplied and outflow of the culture fluid of SB, the quantity of fluid in the culture tank 2 is kept constant, and by regulating the quantity of both supply and outflow per an hour, the bacteria at a given stage in the growth curve of SB can be proliferated selectively. In the tank 4 for separating SB, the culture fluid is filtered to obtain SB and the filtrate, the SB being sent to the tank 5 for forming pore. The filtrate is transferred to the tank 6 for culturing LB, and simultaneously the basal medium is supplied from the medium tank 1 to the tank 6 for culturing LB by the medium delivery pump 3B, and then LB is inoculated into the mixture of the filtrate and basal medium. After proliferating LB, the culture fluid containing LB is transferred to the tank 7 for culturing BB and LB by the delivery pump 3C, and simultaneously the basal medium is supplied from the medium tank 1 to the tank 7 and BB is inoculated. To the tank 7 for culturing BB and LB, mixed gas comprising nitrogen gas and carbon dioxide is supplied from a gas cylinder 8, and BB and LB are proliferated under an anaerobic condition. Then, the culture fluid is transferred to the tank 9 to form spores of BB, and after the spore formation the mixture of LB and BB are separated from the culture fluid by a centrifuge 10.

EXAMPLE 2

Another method of the present invention, which is carried out in continuous process, will be illustrated hereinbelow.

(1) Kinds of activated bacteria
    *Lactobacillus acidophilus* for LB
    *Bacillus subtilis* for SB
    *Clostridium acetobutyricum* for BB
(2) Composition and property of the basal medium
    Milk casein         0.5%
    Potato starch       10.0%
    pH                  7.0 (CS medium)
(3) Process The basal medium was employed after sterilizing by an autoclave and cultivation was accomplished at 37° C.

Ten liters of basal medium was added into 10 l in volume of the tank for culturing SB and the SB were proliferated at 37° C. under aerobic conditions. From 6 hours after starting incubation the basal medium was supplied to the tank for culturing SB at a ratio of 1000 ml/hr and simultaneously the cultured fluid of SB was transferred to the tank for separating SB at a ratio of 1000 ml/hr, and the SB were removed.

Subsequently, to the 100 l in volume of the tank for culturing LB, in which 50 l of the basal medium had been introduced in advance, the basal medium and the filtrate of SB were supplied at a ratio of 5000 ml/hr and 1000 ml/hr, respectively, thus LB were proliferated at 37° C. under aerobic conditions.

From 6 hours after starting cultivation of LB, to the 1000 l in volume of the tank for culturing BB and LB, in which 500 l of the basal medium had been introduced in advance, the basal medium and the cultured fluid of LB were supplied at a ratio of 50,000 ml/hr and 6,000 ml/hr, respectively, and the mixed gas comprising $CO_2$ (10%) and $N_2$ gas (90 %) was passed into the culture tank. Then the BB were inoculated and proliferated at 37° C. under anaerobic conditions. The culture fluid of both BB and LB was transferred to the tank for forming spores of BB at of 56,000 ml/hr, and after the spore formation the mixture of LB and BB were separated from the cultured fluid.

(4) Bacteria count

After the conditions of culture became stable in such a continuous cultivation, samples were harvested from the tanks for culturing LB and for BB and LB, and counts of both LB and BB per 1 ml of the sample were accomplished on a GYP agar plate. The results are shown in the following Table A, in which the bacteria proliferated under the condition (A) or (B) are also included: in (A) LB are proliferated in the culture tank for LB which is supplied with the basal medium alone, and in (B) the single cultivation of BB is carried out in the culture tank for BB and LB, but supplied with the basal medium alone. In the Comparative Example the quantity of the basal medium supplied is the same as the example of the invention.

TABLE A

|  | LB (Aerobic Culture) | BB (Anaerobic Culture) |
|---|---|---|
| Example | $3.5 \times 10^8$ | $9.7 \times 10^8$ |
| Comparative Example A | $<10^6$ | — |
| Comparative Example B | — | $8.4 \times 10^7$ |

The results showed that the medium containing filtrate of the culture fluid of SB increased the LB count in the culture fluid more than 100 times as compared with the medium without the filtrate (Comparative Example A). A mixed culture of BB with LB was shown to increase the BB count about twelve times as compared with the single culture of BB (Comparative Example B).

The symbiotic mixture of three kinds of bacteria in the present invention contains active bacteria useful for human and animals as an effective component and hence, in case that it is applied to, for example, a medicament for bowel movement, it will offer a high safety.

Furthermore, as to a medicament for bowel movement which is illustrated in Example 1, results on safety (toxicity) tests in mice will be described hereinafter.

Safety (toxicity) tests of "medicament for bowel movement" in oral administration in mice:
I. Materials and Methods:
1. Preparation
   "Medicament for bowel movement"
2. Animal
   ICR mice (male), Japan Charles River Co., were employed for tests. The body weight at a start of the test was 26 to 29 gram.
3. Breeding method and environment Twenty four male mice were reared in the animal breeding room, Department of Agricultural Chemistry, Tokyo University of Agriculture. The room was adequately ventilated and the humidity kept at 60±5% and temperature at 22°±2° C. Six mice were housed in a breeding cage (for mice) for 1 week before the test and observed for 1 week after administration.

4. Examination groups

One group consists of eight mice, and this test is composed of three groups: an ordinary dose group (I), 30 times the ordinary dose group (II), and animal control group.

5. Method for preparation of the medicament and for administration

In the ordinary dose group, "medicament for bowel movement" was suspended in distilled water in a concentration of 6 mg/ml, and in the group of 30 times the ordinary dose 180 mg/ml. In the animal control group the distilled water alone was orally administered in an amount of 0.5 ml/mouse using a stomach tube. Incidentally, a single oral administration was accomplished.

6. Observation items and clinical laboratory examination (blood examination) items Following administration, the form of feces, movement, increase in body weight were observed every day. After the test was completed, mice were sacrificed and the blood was collected by heart puncture, and blood examination was done, in which a red blood cell count and hemoglobin count were accomplished.

7. Autopsy findings

After the tests were completed, mice were sacrificed and an autopsy was conducted.

II. Results

1. Characteristics of feces (macroscopic observation)

After the administration, any abnormality in color, shape, moisture, and volume was not observed in both the ordinary dose group and 30 times the ordinary dose group, as compared with the control group. There was no change in those from the post-administration to the time of completion of test.

2. Movement

Immediately after an oral administration, some mice got a shock but soon recovered, and other changes did not appear after that, bristle and bleeding were not observed either.

3. Survival

All mice in the groups survived without any trouble until the time of completion of test.

4. Change in body weight

As shown in Table 1, normal change in body weight was observed from the administration to the time of completion of test.

TABLE 1

| Group | Body Weight Before Administration | Body Weight After Administration (g) | | | | | | |
|---|---|---|---|---|---|---|---|---|
| | | 1 (day) | 2 | 3 | 4 | 5 | 6 | 7 |
| Ordinary Dose | 26.5 g | 26.9 | 27.4 | 27.9 | 28.1 | 28.6 | 28.9 | 29.2 |
| 30 Times The Ordinary Dose | 27.0 g | 27.6 | 27.9 | 28.6 | 29.2 | 29.9 | 30.3 | 30.8 |

TABLE 1-continued

| Group | Body Weight Before Administration | Body Weight After Administration (g) | | | | | | |
|---|---|---|---|---|---|---|---|---|
| | | 1 (day) | 2 | 3 | 4 | 5 | 6 | 7 |
| Control | 28.3 g | 28.9 | 29.4 | 29.9 | 30.6 | 30.9 | 31.7 | 32.1 |

5. Blood examination

Red blood cell (R.B.C.) count and hemoglobin count will be shown in Table 2.

TABLE 2

| | Strains | R.B.C. ($\times 10^4$) | Hemoglobin (mg/dl) |
|---|---|---|---|
| Ordinary Dose | 1-1 | 250 | 13.35 |
| | 2 | 989 | 13.58 |
| | 3 | 510 | 13.23 |
| | 4 | 942 | 14.67 |
| | 5 | 1255 | 14.32 |
| 30 Times The Ordinary Dose | 2-1 | 1072 | 13.76 |
| | 2 | 929 | 12.61 |
| | 3 | 830 | 13.08 |
| | 4 | 850 | 12.23 |
| | 5 | 993 | 12.20 |
| Control | 3-1 | 538 | 14.56 |
| | 2 | 999 | 15.31 |
| | 3 | 1214 | 18.07 |
| | 4 | 649 | 17.10 |
| | 5 | 824 | 17.25 |
| Experiment* Value | | 675 (524–1063) | 13.9 (11.8–15.6) |

*M. Okunogi "Usage and Technique of Experimental Animals"

* M. Okunogi "Usage and Technique of Experimental Animals"

As shown in tables, values of the respective groups were not so different from the experiment value, therefore the same event is considered to take place. As for the red blood cell count, there is a dispersion on the basis of technical errors and individual difference, but it is almost within the range of experimental value.

6. Autopsy findings

After the completion of test, mice were sacrificed and an autopsy was carried out. Findings will be shown in the accompanying sheet.

III. Considerations

"Medicament for bowel movement" was administered to mice in the test group I at an ordinary dose and in the test group II at 30 times as much dose as in group I, and general clinical findings and pathological observations were accomplished. Safety of the medicament was investigated and the following results were obtained.

1. Pathological findings

Macroscopic findings of general appearance

In any of test group I, II, and control group, no abnormality in items such as nutrition, gloss of hair and postural discharge from, e.g. nostril and anus was observed.

2. Macroscopic findings of organs (autopsy)

In No. 4 mice of the test group, a slight redness in the intestine (duodenum) was observed but the lesion of bleeding in the mucosal area (slice of the intestine) was not detected.

In No. 9 mice of the control group, all lobes of the liver lack normal color and anemia was detected. The results mentioned above will be summarized in Table 3.

3. There were no problems to be raised on safety.

TABLE 3

Monitor Animal and Examination Items

| Division | Animal No. | Item | Mouse Strain | Sex | Age at Autopsy (day) | Body Weight at Autopsy (g) | Medicament Dose | Examination Item Nutrition | Macroscopic Findings of General Appearance Gloss of Hair | Pustural Discharge |
|---|---|---|---|---|---|---|---|---|---|---|
| Experiment | (I) | 1 | ICR | ♂ | 42 | 28.6 | Ordinary Dose | | Abnormality not detected | |
| | | 2 | | | | 26.5 | | | | |
| | | 3 | | | | 27.5 | | | | |
| | (II) | 4 | ICR | ♂ | 42 | 30.4 | 30 Times The ordinary Dose | | Abnormality not detected | |
| | | 5 | | | | 31.5 | | | | |
| | | 6 | | | | 30.8 | | | | |
| Control | | 7 | ICR | ♂ | 42 | 31.7 | | | Abnormality not detected | |
| | | 8 | | | | 33.0 | | | | |
| | | 9 | | | | 32.0 | | | | |

Examination Item — Macroscopic Findings of Organ (Autopsy)

| Division | Animal No. | Item | Intrathoracic Location of Organ | Change in Pleura | Change in Organ | Intraperitoneum Location of Organ | Change in Peritoneum | Change in Organ |
|---|---|---|---|---|---|---|---|---|
| Experiment | (I) | 1 | Abnormality not detected | | | Abnormality not detected | | |
| | | 2 | | | | | | |
| | | 3 | | | | | | |
| | (II) | 4 | Abnormality not detected | | | Abnormality not detected | | 4. (Intestine) A slight redness was detected in the duodenum. But bleeding in the mucosal area was not macroscopically observed. |
| | | 5 | | | | | | |
| | | 6 | | | | | | |
| Control | | 7 | Abnormality not detected | | | Abnormality not detected | | 9. (Liver) All lobes lack normal color. Anemia was detected. |
| | | 8 | | | | | | |
| | | 9 | | | | | | |

I claim:

1. A mixture of bacteria consisting essentially of:
   (a) a lactic acid producing bacteria selected from a member of the group consisting of Streptococcus faecalis, Streptococcus faecium, Streptococcus lactis, Streptococcus thermophilus, Lactobacillus bulgaricus, Lactobacillus jugurt, Lactobacillus acidophilis, Lactobacillus plantarum, Lactobacillus bifidus, Bifidobacterium bifidum, Bifidobacterium infantis and Bifidobacterium longum,
   (b) a saccharifying bacteria selected from a member of the group consisting of Bacillus mesentericus, Bacillus subtilis, and Bacillus natto, and
   (c) a butyric acid producing bacteria selected from a member of the group consisting of Clostridium butyricum and Clostridium acetobutyricum
in a proportion of 1 to 8 parts by weight of saccharifying bacteria and 1 to 8 parts by weight of butyric acid producing bacteria per part by weight of lactic acid producing bacteria.

2. A mixture of three kinds of bacteria according to claim 1, in which the lactic acid producing bacterium is Streptococcus faecalis, the saccarificating bacterium is Bacillus mesentericus, and the butyric acid producing bacterium is Clostridium butyricum.

3. A mixture of bacteria according to claim 1 or 2 in which the butyric acid producing bacteria and the saccharifying bacteria are employed after spore formation.

4. A pharmaceutical composition useful for the maintenance and recovery of intestinal flora comprising a mixture of
   (a) a lactic acid producing bacteria selected from a member of the group consisting of Streptococcus faecalis, Streptococcus faecium, Streptococcus lactis, Streptococcus thermophilus, Lactobacillus bulgaricus, Lactobacillus jugurt, Lactobacillus acidophilis, Lactobacillus plantarum, Lactobacillus bifidus, Bifidobacterium bifidum, Bifidobacterium infantis and Bifidobacterium longum,
   (b) a saccharifying bacteria selected from a member of the group consisting of Bacillus mesentericus, Bacillus subtilis, and Bacillus natto, and
   (c) A butyric acid producing bacteria selected from a member of the group consisting of Clostridium butyricum and Clostridium acetobutyricum
in a proportion of 1 to 8 parts by weight of saccharifying bacteria and 1 to 8 parts by weight of butyric acid producing bacteria per part by weight of lactic acid producing bacteria, said mixture containing $10^6$ to $10^{10}$ bacteria per g in combination with a pharmaceutically acceptable carrier.

* * * * *